(12) United States Patent
Fairfax et al.

(10) Patent No.: US 8,697,697 B2
(45) Date of Patent: Apr. 15, 2014

(54) PYRAZOLE DERIVATIVES AS ERK INHIBITORS

(75) Inventors: David Fairfax, Slingerlands, NY (US); Russell Joseph Deorazio, Schenectady, NY (US)

(73) Assignee: Kinentia Biosciences LLC, Rensselaer, NY (US)

( * ) Notice: Subject to any disclaimer, the term of this patent is extended or adjusted under 35 U.S.C. 154(b) by 0 days.

(21) Appl. No.: 13/977,948

(22) PCT Filed: Jan. 3, 2012

(86) PCT No.: PCT/US2012/020074
§ 371 (c)(1),
(2), (4) Date: Sep. 12, 2013

(87) PCT Pub. No.: WO2012/094313
PCT Pub. Date: Jul. 12, 2012

(65) Prior Publication Data
US 2014/0011806 A1    Jan. 9, 2014

Related U.S. Application Data

(60) Provisional application No. 61/429,497, filed on Jan. 4, 2011.

(51) Int. Cl.
| | |
|---|---|
| *A01N 43/66* | (2006.01) |
| *A61K 31/53* | (2006.01) |
| *A01N 43/58* | (2006.01) |
| *A01N 43/60* | (2006.01) |
| *A61K 31/50* | (2006.01) |
| *A01N 43/42* | (2006.01) |
| *A61K 31/44* | (2006.01) |
| *C07D 491/02* | (2006.01) |
| *C07D 498/02* | (2006.01) |
| *C07D 251/00* | (2006.01) |
| *C07D 239/70* | (2006.01) |
| *C07D 241/36* | (2006.01) |

(52) U.S. Cl.
USPC ..... 514/241; 514/250; 514/252.1; 514/258.1; 514/300; 544/180; 544/253; 544/349; 546/113

(58) Field of Classification Search
USPC ............ 546/113; 514/241, 250, 252.1, 258.1, 514/300; 544/180, 253, 349
See application file for complete search history.

(56) References Cited

U.S. PATENT DOCUMENTS

| | | |
|---|---|---|
| 2008/0021026 A1 | 1/2008 | Kahraman et al. |
| 2010/0144730 A1* | 6/2010 | Lind et al. .................. 514/234.5 |
| 2010/0160317 A1 | 6/2010 | Tang et al. |

OTHER PUBLICATIONS

International Search Report for PCT/US2012/020074 dated May 29, 2012.

* cited by examiner

*Primary Examiner* — Niloofar Rahmani
(74) *Attorney, Agent, or Firm* — Heslin Rothenberg Farley & Mesiti P.C.

(57) ABSTRACT

This invention describes substituted pyrazole derivatives of Formula I

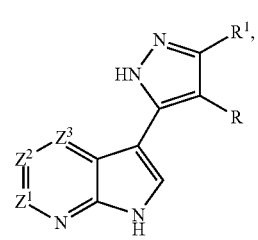

and methods of making and using the compounds. These compounds have utility in the treatment of conditions or diseases in which modification of the activity of ERK would have a positive therapeutic outcome, for instance various cancers, psoriasis and actinic keratosis.

14 Claims, 2 Drawing Sheets

PYRAZOLE DERIVATIVES AS ERK INHIBITORS

CROSS REFERENCE TO RELATED APPLICATIONS

This application is a U.S. National Phase filing under 35 U.S.C. 371 of International Application PCT/US2012/020074, filed Jan. 3, 2012, and published as WO 2012/094313 on Jul. 12, 2012. PCT/US2012/020074 claims priority of U.S. provisional application 61/429,497, filed Jan. 4, 2011. The entire contents of each of the prior applications are hereby incorporated herein by reference.

FIELD OF THE INVENTION

This invention describes a series of substituted pyrazole derivatives that bind to the Extra-cellular Signal Regulated Kinase (ERK). These compounds have utility in the treatment of conditions or diseases in which modification of the activity of ERK would have a positive therapeutic outcome, for instance various cancers, psoriasis and actinic keratosis.

BACKGROUND OF THE INVENTION

The Mitogen-activated Protein (MAP) Kinase Pathway is a key signaling pathway from the cell surface to the nucleus. This signaling cascade controls complex biological processes, such as embryogenesis, differentiation, proliferation, homeostasis and acute hormonal response mechanisms [*Endocr. Rev.* (2001), 22, 153; *Adv. Cancer Res.* (1998) 74, 49]. This transduction of information is mediated by the MAP family of kinases that phosphorylate and regulate a wide range of substrates including transcription factors, cytoskeletal elements and other kinases. Intense interest in protein kinases as drug targets has developed over the past few years, the MAP Kinase pathway being of particular focus. For example, inhibitors of B-Raf kinase and MEK have been developed, with the B-Raf inhibitor Sorafenib having been recently commercialized. ERK appears to be a pivotal junction point in the MAP kinase cell-signaling cascade, being the last cytosolic member of the pathway that translocates to the nucleus and instigates the transcription process. Additionally, significant evidence for MAP kinase independent ERK activation pathways in melanoma and other cell lines have been reported [J. Clin. Pathol. (2005), 58, 1163; Oncogene, (1997), 14, 1635; *Biochem. Biophys. Research Comm.* (2005), 329, 266; *Am. J. Physio. Cell. Physiol.* 2002, 283, C282; *Cell Signal.* (2010), 9, 1369], a mechanism by which inactivation of upstream kinase inhibitors may occur. For example, it has been reported that ERK trans-activation pathways are the reasons for the resistance observed during B-Raf kinase targeted melanoma therapy [*Br. J. Cancer.* (2010), 102, 1724].

SUMMARY OF THE INVENTION

The compounds of this invention have utility in the treatment of conditions or diseases in which modification of the activity of ERK would be expected to have a positive therapeutic outcome. The compounds of this invention are useful for the treatment of a variety of hyperproliferative disorders including but not limited to melanoma, psoriasis, actinic keratosis, restenosis and cancers of the brain, lung, breast, ovaries, pancreas, prostrate and colon. Additionally, there is good evidence that the compounds of the invention are useful for the treatment of a disorder wherein a suppression of inflammation is desirable, i.e. as anti-inflammatory agents. Such disorders include but are not limited to rheumatoid arthritis, chronic obstructive pulmonary disease, fibrotic disease and Crohn's disease.

In one aspect the invention relates to compounds of formula I

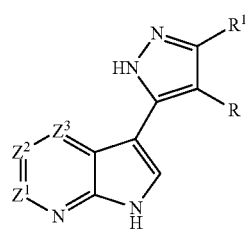

wherein

R is selected from hydrogen, $(C_1-C_{12})$hydrocarbon, $(C_3-C_{10})$carbocycle and heteroaryl, each of which may be optionally substituted by one or more substituents selected from hydrogen, $(C_1-C_6)$hydrocarbon, halogen, $(C_1-C_6)$alkoxy and $(C_1-C_6)$alkylthio;

$R^1$ is hydrogen or $(C_1-C_6)$hydrocarbon;

$Z^1$ is $CR^a$;

$Z^2$ and $Z^3$ are each chosen independently from N and $CR^a$;

$R^a$ is chosen independently in each occurrence from hydrogen, $(C_1-C_6)$alkyl and $(CR^3R^4)_n$—$R^2$, wherein one or more $CR^3R^4$ may be replaced by O, $NR^{10}$, S or C=O;

$R^2$ is $OR^5$ or $NR^5R^6$;

$R^3$ is independently selected from hydrogen and $(C_1-C_6)$ hydrocarbon;

$R^4$ is independently selected from hydrogen and $(C_1-C_6)$ hydrocarbon;

$R^5$ is independently selected from hydrogen and $(C_1-C_6)$ hydrocarbon;

$R^6$ is independently selected from hydrogen and $(C_1-C_6)$ hydrocarbon, or $R^5$ and $R^6$, together with the nitrogen to which they are attached, may form a 3- to 10-membered monocyclic or bicyclic heterocycle;

$R^{10}$ is selected from hydrogen and a $(C_1-C_{10})$hydrocarbon optionally substituted with halogen, $(C_1-C_6)$alkyl, $(C_1-C_6)$ alkoxy or hydroxy$(C_1-C_6)$alkyl; or $R^3$ and $R^{10}$, together with the nitrogen to which they are attached, may form a 3- to 10-membered monocyclic or bicyclic heterocycle; and n is selected from 1, 2, 3, 4, 5, 6, 7, 8 and 9.

In one embodiment, the invention relates to pharmaceutical compositions comprising at least one compound of the invention and a pharmaceutically acceptable carrier.

In one embodiment, the invention relates to a method of inhibiting the extracellular signal-regulated kinase comprising bringing an extracellular signal-regulated kinase into contact with a compound or a composition of the invention.

In one embodiment, the invention relates to a method of inhibiting MMP-1 comprising bringing MMP-1 into contact with a compound or a composition of the invention.

In one embodiment, the invention relates to a method of inhibiting keratinocyte growth comprising administering a compound or a composition of the invention.

In one embodiment, the invention relates to a method of inhibiting abnormal cell growth or treating a hyperproliferative disorder by administering an effective dose of a compound or a composition of the invention to a subject in need thereof.

In one embodiment, the invention relates to a method of treating a disease or condition ameliorated by the inhibition of extracellular signal-regulated kinase comprising administering an effective dose of a compound or a composition of the invention to a subject in need thereof.

In one embodiment, the invention relates to a process for preparing a compound of formula III

III said process comprising the steps of:

a) reacting a compound of formula IV

IV with $CH_3NHOCH_3$ and TIPS-Cl to form a compound of formula V

V b) reacting a compound of formula V with a compound of formula VI

VI wherein $R^{30}$ is selected from halogen and methyl, and $R^{31}$ is selected from Cl, Br, I, toluenesulfonyl, benzenesulfonyl, methanesulfonyl and triflate to form a compound of formula VII

VII reacting a compound of formula VII with Brederecks Reagent and hydrazine and cleaving with acid to form a compound of formula III.

In some of these embodiments, the reaction of a compound of formula IV and $CH_3NHOCH_3$ is carried out in the presence of a diimide and 1-hydroxy-1H-benzotriazole.

In one embodiment, the invention relates to a process for preparing a compound of formula VIII

VIII wherein A is selected from O, S and $NR^{32}$;

Z is chosen from hydrogen, $(C_1-C_6)$alkyl and $[(C_1-C_{10})$alkyl]-$R^8$, wherein one or more $CH_2$ of the alkyl may be replaced by O, $NR^{10}$, S or C=O, and wherein $R^8$ is protected OH or protected $NHR^{11}$;

$R^{10}$ and $R^{11}$ are independently selected in each instance from hydrogen and $(C_1-C_6)$alkyl; and $R^{30}$ is selected from halogen and methyl $R^{32}$ is hydrogen or a $(C_1-C_6)$ hydrocarbon;

comprising the steps of a) reacting a compound of formula III

III with an oxidant to form a compound of formula IX

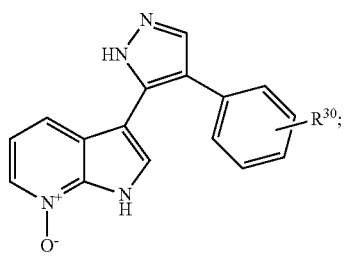

b) reacting a compound of formula IX with an activating agent to form a compound of formula X

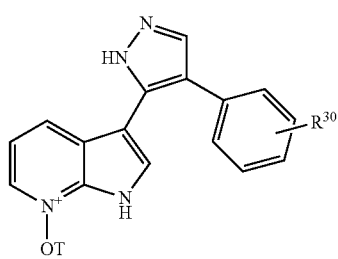

wherein T is selected from methyl or $(C_4H_8N)_3P^+$;
and reacting a compound of formula X with H-AZ to form a compound of formula VIII,
wherein A and Z are defined as above.

In some of these embodiments, the oxidant is MCPBA and the activating agent is dimethylsulfate or Bromo-tris-pyrrolidinophosphonium hexafluorophosphate.

DETAILED DESCRIPTION OF THE INVENTION

Figure 1:
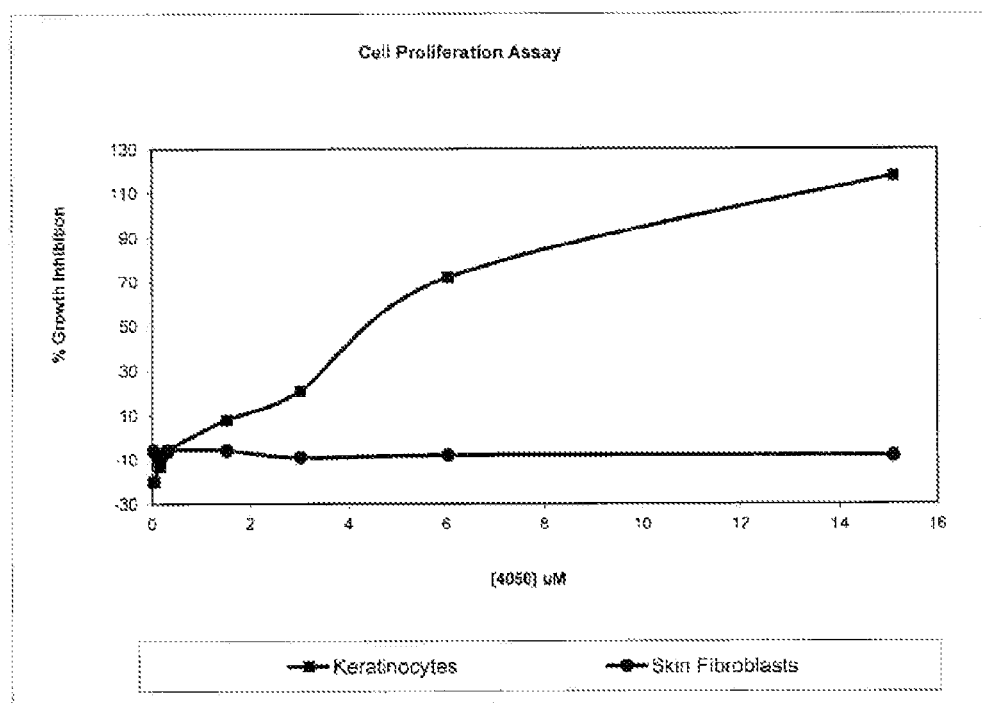
FIG. 1 shows a graph which demonstrates the effect of an embodiment of the invention on keratinocyte and skin fibroblast proliferation.

Compounds of the invention have been found to inhibit the activity of ERK. As such, they have utility for the treatment of a variety of diseases in which disruption or inhibition of the MAP kinase signaling pathway could be expected to have a positive therapeutic effect. The compounds also have utility in the treatment of disease states in which non-MAP kinase trans-activation of ERK is a secondary response or resistance mechanism. In addition to their ability to inhibit ERK, compounds of the invention have also been found to selectively inhibit the proliferation of human keratinocytes over human skin fibroblasts. The effect of various concentrations of Example 1 of the invention to inhibit the proliferation of human keratinocytes and skin fibroblasts is depicted graphically in FIG. 1. The observed selectivity of Example 1 is particularly advantageous for the treatment of skin diseases where the inhibition of production of keratinocytes is desired, but the production of skin fibroblasts is unaffected. One example of skin disease is psoriasis, in which current topical steroid therapies are unselective, and prolonged use results in thinning or atrophy of the lower dermis necessitating treatment withdrawal. Thus, compounds of the invention have the potential to treat a disease state, such as psoriasis, in which hyper-proliferation of keratinocytes is a causative effect and be less prone to side-effects associated with lower dermal disruption or atrophy.

The compounds of the invention have also been founds to inhibit the production of MMP-1 or collagenase in skin fibroblasts. Analysis of MMP-1 expression by human skin fibroblasts via Western blot analysis after exposure to Example 1 of the invention revealed that at higher concentrations significant reduction in collagenase production was observed, despite minimal effect on fibroblast proliferation. The ability of Example 1 of the invention to inhibit the production of MMP-1 in skin fibroblasts, and the associated Western blot analysis, is depicted graphically in FIG. 2. Thus, the compounds of the invention also have the potential to treat a disease or condition in which the down-regulation of MMP-1 could be expected to have a positive therapeutic effect.

In one aspect the invention relates to compounds of formula I

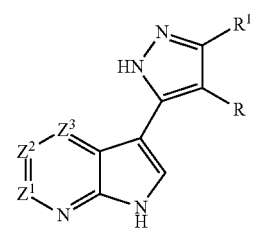

In some embodiments of the invention, R is hydrogen. In other embodiments, R is $(C_1-C_{12})$hydrocarbon. For instance, R may be $(C_1-C_{12})$alkyl, $(C_1-C_{12})$alkenyl or $(C_1-C_{12})$alkynyl. In still other embodiments, R is $(C_3-C_{10})$carbocycle. For instance, R may be phenyl. In yet other embodiments, R is heteroaryl. For instance, R may be thiophene, pyridine, furan or pyrrole. When R is not hydrogen, it may be substituted by one or more substituents selected from hydrogen, $(C_1-C_6)$hydrocarbon, halogen, $(C_1-C_6)$alkoxy and $(C_1-C_6)$alkylthio. In some embodiments of the invention, R is phenyl substituted by halogen or methyl. In some embodiments of the invention, R is phenyl substituted by chlorine. In still other embodiments, R is phenyl substituted in the 3-position. In yet other embodiments, R is phenyl substituted by chlorine in the 3-position.

In some embodiments of the invention, $R^1$ is hydrogen. In other embodiments of the invention, $R^1$ is $(C_1-C_6)$hydrocarbon. For instance, in some embodiments, $R^1$ is methyl.

$R^a$ is chosen independently in each occurrence. In some embodiments of the invention, $R^a$ is hydrogen. In some embodiments of the invention, $R^a$ is $(C_1-C_6)$alkyl. In some embodiments of the invention, $R^a$ is $(CR^3R^4)_nR^2$. In some embodiments of the inventions, one or more $CR^3R^4$ may be replaced by O, $NR^{10}$, S or C=O.

In some embodiments of the invention, $R^3$ is hydrogen. In some embodiments of the invention, $R^3$ is $(C_1-C_6)$hydrocarbon.

In some embodiments of the invention, $R^4$ is hydrogen. In some embodiments of the invention, $R^4$ is $(C_1-C_6)$hydrocarbon.

In some embodiments of the invention, $R^2$ is $OR^5$. In some embodiments of the invention, $R^2$ is $NR^5R^6$.

In some embodiments of the invention, $R^5$ is hydrogen. In some embodiments of the invention, $R^5$ is $(C_1-C_6)$hydrocarbon.

In some embodiments of the invention, $R^6$ is hydrogen. In some embodiments of the invention, $R^6$ is $(C_1-C_6)$hydrocarbon.

In some embodiments of the invention, $R^5$ and $R^6$, together with the nitrogen to which they are attached, may form a 3- to 10-membered monocyclic or bicyclic heterocycle.

In some embodiments of the invention, $R^2$ is OH. In other embodiments of the invention, $R^2$ is $NH_2$. In still other embodiments of the invention, $R^2$ is morpholino, piperazinyl or 4-methylpiperazinyl.

In some embodiments of the invention, $R^{10}$ is hydrogen. In some embodiments of the invention, $R^{10}$ is a $(C_1-C_{10})$hydrocarbon. For instance, $R^{10}$ may be methyl, ethyl, propyl, t-butyl, benzyl or phenyl. When $R^{10}$ is a $(C_1-C_{10})$hydrocarbon, it may be optionally substituted with halogen, $(C_1-C_6)$alkyl, $(C_1-C_6)$alkoxy or hydroxy$(C_1-C_6)$alkyl. Illustrative, non-limiting examples may be methoxy, fluoro, chloro, hydroxymethyl or hydroxyethyl. In still other embodiments of the invention, $R^3$ and $R^{10}$, together with the nitrogen to which they are attached, may form a 3- to 10-membered monocyclic or bicyclic heterocycle. For instance, $R^3$ and $R^{10}$ may form a piperidinyl.

In some embodiments of the invention, the value of n is selected from any integer between 1 and 9.

In some embodiments of the invention, $Z^1$ is $CR^a$.

In some embodiments of the invention, $Z^2$ and $Z^3$ are each chosen independently from N and $CR^a$. In some embodiments, both $Z^2$ and $Z^3$ are N. In some embodiments, one of $Z^2$ and $Z^3$ is N and one is $CR^a$. In some embodiments, both $Z^2$ and $Z^3$ are $CR^a$.

In some embodiments of the invention, $Z^1$, $Z^2$ and $Z^3$ are each $CR^a$. In some of these embodiments, $Z^2$ and $Z^3$ are each CH. In still other embodiments, $Z^1$, $Z^2$ and $Z^3$ are each CH. In other embodiments, $Z^2$ and $Z^3$ are each CH and $Z^1$ is C—W—$(CR^3R^4)_n$OH. In other embodiments, $Z^2$ and $Z^3$ are each CH and $Z^1$ is C—W—$(CR^3R^4)_n$NH$_2$.

In some embodiments of the invention, W is O. In other embodiments, W is NR$^{10}$. In some embodiments, W is NH. In still other embodiments, W is S. In yet other embodiments, W is C═O.

In some embodiments of the invention, $Z^1$ is CNR$^{10}$(CR$^3$R$^4$)$_n$OH. In other embodiments of the invention, $Z^1$ is CNR$^{10}$(CR$^3$R$^4$)$_n$N(CH$_3$)$_2$. In still other embodiments of the invention, $Z^1$ is CNR$^{10}$(CR$^3$R$^4$)$_n$N(CH$_3$)$_2$. In yet other embodiments of the invention, $Z^1$ is CNR$^{10}$(CR$^3$R$^4$)$_n$C(═O)OH.

In one aspect the invention relates to compounds of formula Ia

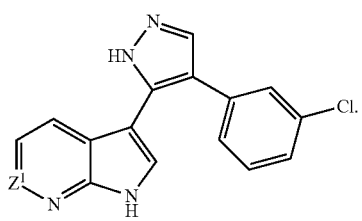

Ia

In some of these embodiments of the invention, $Z^1$ is CH. In other embodiments, $Z^1$ is C—W—$(CR^3R^4)_n$OH. In still other embodiments of the invention, $Z^1$ is C—W—$(CR^3R^4)_n$NH$_2$.

In some embodiments, the invention relates to a method of inhibiting keratinocyte growth comprising administering a compound or a composition of the invention. In some of these embodiments, the method of inhibiting is an in vitro method. In other embodiments, the method of inhibiting is an in vivo method.

In some embodiments, the invention relates to a method of inhibiting abnormal cell growth or treating a hyperproliferative disorder by administering an effective dose of a compound or a composition of the invention to a subject in need thereof. In some of these embodiments, the hyperproliferative disorder is selected from psoriasis, actinic keratosis and melanoma.

In some embodiments, the invention relates to a method of treating a disease or condition ameliorated by the inhibition of extracellular signal-regulated kinase comprising administering an effective dose of a compound or a composition of the invention to a subject in need thereof. In some of these embodiments, the effective dose is administered topically.

In some embodiments, the activating agent is dimethylsulfate. In other embodiments, the activating agent is Bromo-tris-pyrrolidinophosphonium hexafluorophosphate. Other potential activating agents may include diethylsulfate, tosyl chloride, tosic anhydride, BrOP (bromo-tris-(dimethylamino) phosphonium hexafluorophosphate), trimethylsilyl triflate or triisopropylsilyl triflate.

DEFINITIONS

Throughout this specification the terms and substituents retain their definitions.

Alkyl is intended to include linear or branched, or cyclic hydrocarbon structures and combinations thereof. A combination would be, for example, cyclopropylmethyl. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like. To be perfectly clear, when a substituent is $(C_1-C_6)$alkyl (or alkylene), it is meant that it can be a straight chain (for instance, methyl or ethyl), a branched chain (e.g., t-butyl), a cycloalkyl (for instance, cyclopropyl or cyclobutyl), or a combination (e.g., methylcyclopropyl). If a substituent is described more specifically, however, it takes on that definition; for instance, a cycloalkyl can only be a cyclic alkyl.

Alkoxy or alkoxyl refers to groups of from 1 to 6 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Similarly, alkylthio refers to groups of from 1 to 6 carbon atoms of a straight, branched, or cyclic configuration and combinations thereof attached to the parent structure through sulfur.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Arylalkyl means an alkyl residue attached to an aryl ring. Examples are benzyl, phenethyl and the like. Heteroarylalkyl means an alkyl residue attached to a heteroaryl ring. Examples include, e.g., pyridinylmethyl, pyrimidinylethyl and the like.

Hydrocarbon means a linear, branched, or cyclic residue comprised of hydrogen and carbon as the only elemental constituents and includes alkyl, cycloalkyl, polycycloalkyl, alkenyl, alkynyl, aryl and combinations thereof. Examples include benzyl, phenethyl, cyclohexylmethyl, camphoryl and naphthylethyl.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene and cyclohexene. Carbocycle, if not otherwise limited, refers to monocycles, bicycles and polycycles.

Heterocycle means a cycloalkyl or aryl residue in which one to four of the carbons is replaced by a heteroatom such as oxygen, nitrogen or sulfur. Heteroaryls form a subset of heterocycles. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like.

The term "halogen" means fluorine, chlorine, bromine or iodine. In one embodiment, halogen may be fluorine or chlorine.

As used herein, the term "optionally substituted" may be used interchangeably with "unsubstituted or substituted". The term "substituted" refers to the replacement of one or more hydrogen atoms in a specified group with a specified radical. In one embodiment, 1, 2 or 3 hydrogen atoms are replaced with a specified radical. In the case of alkyl and cycloalkyl, more than three hydrogen atoms can be replaced by fluorine; indeed, all available hydrogen atoms could be replaced by fluorine.

Some of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

Some of the compounds of the invention may be present as quaternary salts, i.e. cationic species. The term "pharmaceutically acceptable salt" refers to salts whose counter ion (anion) derives from pharmaceutically acceptable non-toxic acids including inorganic acids, organic acids and water (which formally furnishes the hydroxide anion). Suitable pharmaceutically acceptable anions for the compounds of the present invention include hydroxide, acetate, benzenesulfonate (besylate), benzoate, bicarbonate, bisulfate, carbonate, camphorsulfonate, citrate, ethanesulfonate, fumarate, gluconate, glutamate, glycolate, bromide, chloride, isethionate, lactate, maleate, malate, mandelate, methanesulfonate, mucate, nitrate, pamoate, pantothenate, phosphate, succinate, sulfate, tartrate, trifluoroacetate, p-toluenesulfonate, acetamidobenzoate, adipate, alginate, aminosalicylate, anhydromethylenecitrate, ascorbate, aspartate, calcium edetate, camphorate, camsylate, caprate, caproate, caprylate, cinnamate, cyclamate, dichloroacetate, edetate (EDTA), edisylate, embonate, estolate, esylate, fluoride, formate, gentisate, gluceptate, glucuronate, glycerophosphate, glycolate, glycollylarsanilate, hexylresorcinate, hippurate, hydroxynaphthoate, iodide, lactobionate, malonate, mesylate, napadisylate, napsylate, nicotinate, oleate, orotate, oxalate, oxoglutarate, palmitate, pectinate, pectinate polymer, phenylethylbarbiturate, picrate, pidolate, propionate, rhodanide, salicylate, sebacate, stearate, tannate, theoclate, tosylate and the like. The desired salt may be obtained by ion exchange of whatever counter ion is obtained in the synthesis of the quat. These methods are well known to persons of skill. Although pharmaceutically acceptable counter ions will be preferred for preparing pharmaceutical formulations, other anions are quite acceptable as synthetic intermediates. That is, pharmaceutically undesirable anions, such as iodide, oxalate, trifluoromethanesulfonate and the like, may be present when such salts are chemical intermediates. When the compounds of the invention are bisquats, one may employ as counter ions either two monoanionic species (e.g. $Cl_2$) or a single dianionic species (e.g. fumarate). Similarly, one could employ oligoanionic species and make salts having appropriate ratios of quat to counterion, such as (quat)$_3$ citrates. These would be obvious equivalents.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Compounds that contain isotopes $^{11}C$, $^{13}N$, $^{15}O$ and $^{18}F$ are well suited for positron emission tomography. For instance, the 4-fluorine could easily be substituted by $^{18}F$. Radiolabeled compounds of formula I of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the genus (I) that are not already in the possession of the public.

| Abbreviations The following abbreviations and terms have the indicated meanings throughout: | |
|---|---|
| Ac = | acetyl |
| Boc = | t-butyloxy carbonyl |
| Bredereck's Reagent = | tert-Butoxy-bis-(dimethyamino)methane |
| BrOP = | bromo-tris-(dimethylamino) phosphonium hexafluorophosphate |
| Bu = | butyl |
| c- = | cyclo |
| DIPEA = | Diisopropylethylamine |
| DMF = | N,N-dimethylformamide |
| EDC = | 1-(3-(dimethylamino)propyl)-3-ethyl-carbodiimide hydrochloride |
| ERK = | extra-cellular signal regulated kinase |
| EtOAc = | ethyl acetate |
| HOBt = | Hydroxybenzotriazole |
| LiHMDS = | lithium hexamethyldisilazide |
| MAP = | Mitogen-activated Protein |
| m-CPBA = | meta-Chloroperoxybenzoic Acid |
| Me = | methyl |
| MMP = | matrix metalloproteinase |
| NaH = | sodium hydride |
| Ph = | phenyl |
| PhOH = | phenol |
| PyBrOP = | Bromo-tris-pyrrolidino phosphoniumhexafluorophosphate |
| rt = | room temperature |
| sat'd = | saturated |
| TBDMS = | t-butyldimethylsilyl |
| TFA = | trifluoroacetic acid |
| THF = | tetrahydrofuran |
| TIPS = | Triisopropylsilyl |
| TLC = | Thin Layer Chromatography |
| TMS = | trimethylsilyl |

It may happen that residues in the substrate of interest require protection and deprotection during the synthesis procedure. Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is below, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

General Synthetic Methods

Compounds of the invention may be synthesized via the general routes depicted in Scheme 1. Amide formation between 7-azaindole-3-carboxylic acid and N,O-Dimethyl-hydroxylamine followed by TIPS protection under standard conditions affords the corresponding amide 1. Reaction of 1 with an appropriate organometallic reagent affords ketone product 2. Reaction of ketone 2 with tert-Butoxy-bis-(dimethyamino)methane, or the derived anion of 2 with an appropriate acylating agent, affords dicarbonyl equivalent or dicarbonyl compound 3 respectively. Treatment of 3 with hydrazine monohydrochloride and hydrazine monohydrate affords the desired pyrazole 4. Optional oxidation of 4 with m-CPBA affords the corresponding N-oxide 5. This compound can be treated with a strong activating agent, such as dimethylsulfate or PyBrOP, to give the intermediate pyridinium type intermediate, which can be directly reacted with an appropriate nucleophile (AZ-H) to afford the final 6-substituted compounds.

Scheme 1

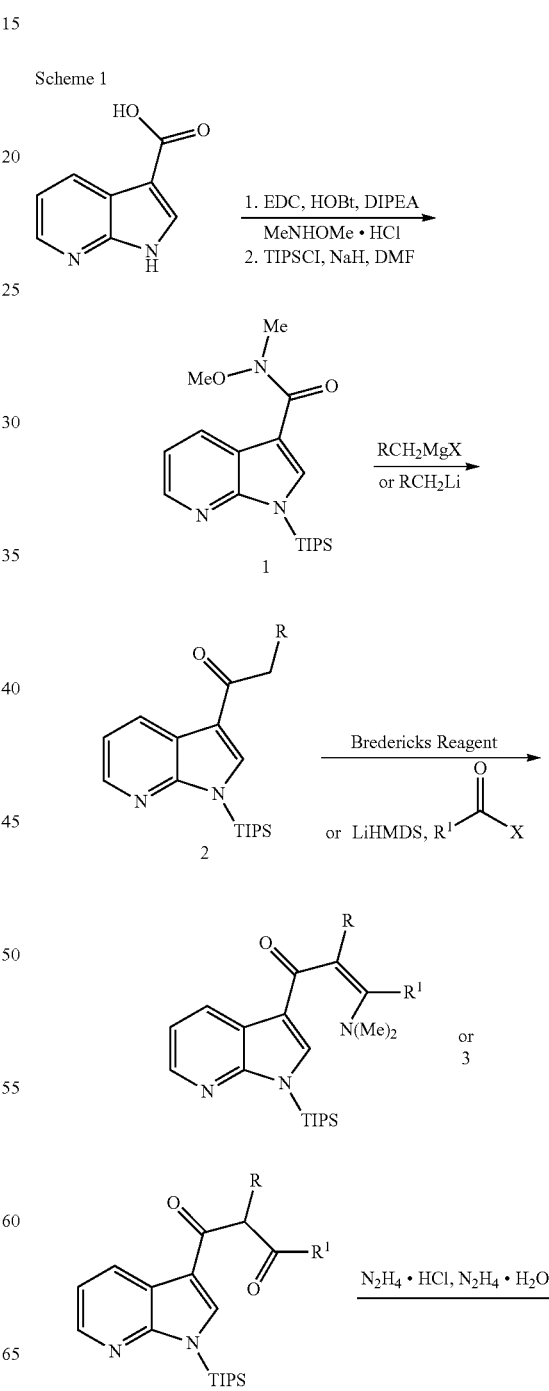

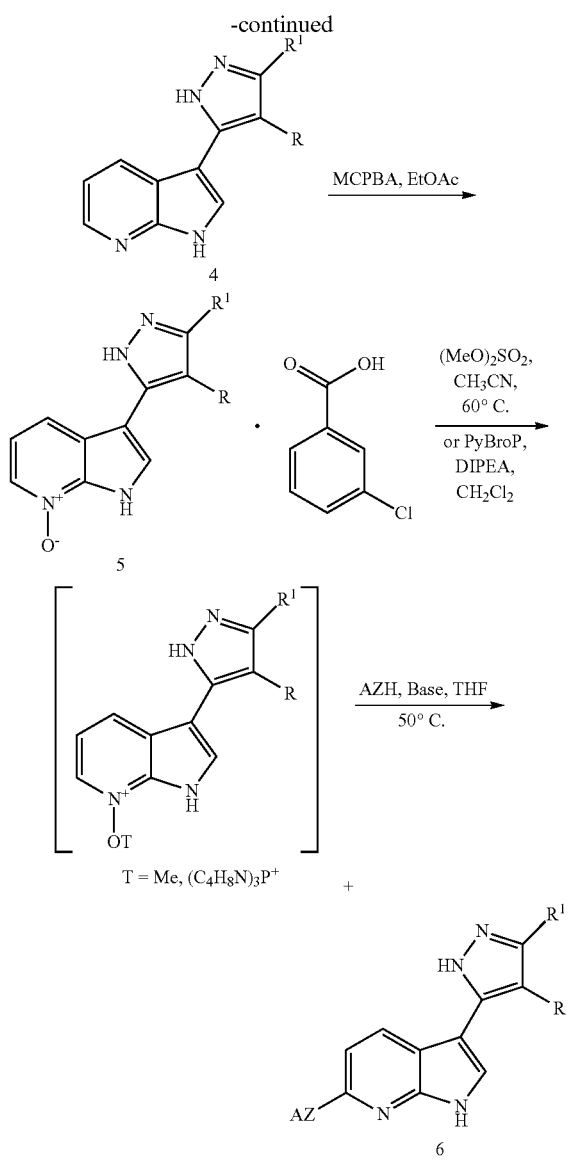

EXAMPLES

Preparation of N-Methoxy-N-methyl-1H-Pyrrolo[2,3-b]pyridine-3-carboxamide

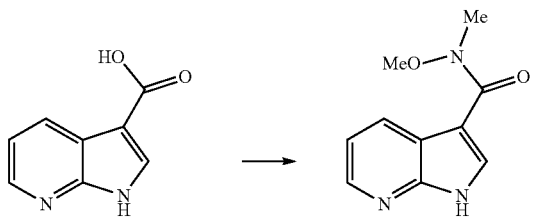 [SMILES: O=C(O)c1c[nH]c2ncccc12 ; CON(C)C(=O)c1c[nH]c2ncccc12]

To a solution of 7-azaindole-3-carboxylic acid (324 mg, 2.00 mmol) in dioxane (10 mL) was added HOAt (300 mg, 2.20 mmol), N,O-Dimethylhydroxylamine hydrochloride (214 mg, 2.00 mmol) and EDC (422 mg, 2.20 mmol). The mixture was stirred at rt for 15 minutes then DIPEA (853 mg, 6.60 mmol) added slowly over 5 minutes. The reaction was then stirred at rt for an additional 18 hrs. The reaction was then poured into 25% ammonium chloride solution (10 mL) and extracted with EtOAc (3×10 mL). The combined extracts were dried over magnesium sulfate, filtered and concentrated to a brown oil. This oil was purified via column chromatography (SiO$_2$, EtOAc) to afford the title compound as a viscous clear oil which solidified on standing. Yield=86%

$^1$H NMR (CDCl$_3$): δ=12.48 (bs, 1H), 8.60 (dd, J=7.9, 1.4 Hz, 1H), 8.24 (bd, J=3.8 Hz, 1H), 8.15 (s, 1H), 7.10 (dd, J=7.9, 4.7 Hz, 1H), 3.66 (s, 3H) and 3.31 ppm (s, 3H).

Preparation of N-Methoxy-N-methyl-1-Triisopropyl-silanyl-1H-pyrrolo[2,3-b]pyridine-3-carboxamide

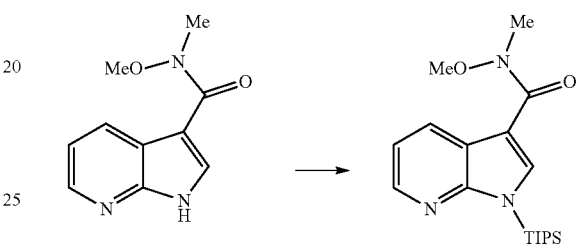

A solution of N-Methoxy-N-methyl-1H-pyrrolo[2,3-b]pyridine-3-carboxamide (300 mg, 1.46 mmol) in DMF (5 mL) was cooled to in an ice bath and sodium hydride (73 mg of 60% dispersion, 1.83 mmol) added in one portion. The mixture was stirred for 5 minutes then triisopropylsilyl chloride (353 mg, 1.83 mmol) added dropwise. The reaction was then stirred for 14 hrs during which time the temperature reached rt. The reaction was then quenched by pouring into a mixture of ice and 25% ammonium chloride solution (50 mL). The resulting mixture was then extracted with EtOAc (2×20 mL) and the combined extracts washed with water (10 mL) and brine (10 mL) then dried over magnesium sulfate. Subsequent filtration and concentration afforded a yellow oil. This crude oil was considered sufficiently pure to carry forward directly. Yield=92%

$^1$H NMR (CDCl$_3$): δ=8.58 (dd, J=7.9, 1.7 Hz, 1H), 8.30 (dd, J=4.7, 1.7 Hz, 1H), 8.10 (s, 1H), 7.15 (dd, J=7.9, 4.7 Hz, 1H), 3.72 (s, 3H), 3.40 (s, 3H), 1.87 (hep, J=7.5 Hz, 3H) and 1.11 ppm (d, J=7.5 Hz, 18H).

General Method 1

The Addition of Grignard Reagents to N-Methoxy-N-methyl-1-triiso-propylsilanyl-1H-pyrrolo[2,3-b]pyridine-3-carboxamide A 0.14 M solution of N-Methoxy-N-methyl-1-triisopropylsilanyl-1H-pyrrolo[2,3-b]pyridine-3-carboxamide in THF was cooled to 0° C. and 1.4 molar equivalents of a solution of the appropriate Grignard reagent in ether or THF added. The reaction was stirred at 0° C. and monitored by TLC until all of the starting material had been consumed. If after 1 hr starting material still remained an additional 0.25 molar equivalents of Grignard reagent was added. Once the starting material had been consumed the reaction was warmed to rt and quenched by the addition of 25% ammonium chloride solution and partitioned between EtOAc and water. The organic was separated and the aqueous re-extracted with EtOAc. The combined extracts were dried over magnesium sulfate, filtered and concentrated. Typically, the crude products obtained were further purified via silica gel column chromatography.

General Method 2

Pyrazole Formation and Triisopropylsilyl Deprotection

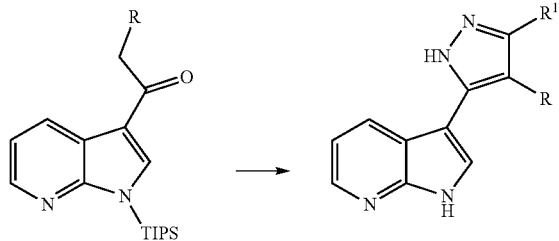

Procedure A: $R^1$=H. To a 0.5 M solution of the appropriate 3-acyl-1-triisopropylsilanyl-1H-pyrrolo[2,3-b]pyridine derivative in DMF was added 1.2 equivalents of Bredereck's reagent and the mixture stirred at room temperature for 16 hrs. After this time the reaction was quenched by the addition of 8 equivalents of hydrazine monohydrochloride. After stirring for 15 minutes at rt hydrazine monohydrate (25 equivalents) was added to the mixture and the reaction heated at 80° C. for 3 hours. After re-cooling to rt the mixture was stirred for a further 3 hrs then poured into water and extracted several times with EtOAc. The combined extracts were washed with water followed by brine then dried over magnesium sulfate, filtered and concentrated. The resulting crude product can be purified by precipitation of the hydrochloride derivative. The crude material was dissolved in methanol and an equal volume of 37% hydrochloric acid added. After stirring for several minutes a precipitate forms. The solids were isolated by filtration and washed with water then dried. If the product could not be isolated in sufficient purity via the hydrochloride derivative then the free base was regenerated and silica gel chromatography utilized.

Procedure B: $R^1$=($C_1$-$C_6$) hydrocarbon. A solution of the appropriate 3-acyl-1-triisopropylsilanyl-1H-pyrrolo[2,3-b] pyridine derivative in THF was added 2.5 equivalents of lithium hexamethyldisilazide and the mixture stirred at 0° C. for 1 hour. The reaction was then treated with 1.2 equivalents of an appropriate acid chloride or anhydride and the solution stirred and slowly warmed to room temperature. The reaction was quenched by the addition of 8 equivalents of hydrazine monohydrochloride. After stirring for 15 minutes at rt hydrazine monohydrate (25 equivalents) was added to the mixture and the reaction heated to reflux for 3 hours. After re-cooling to rt the mixture was poured into water and extracted several times with EtOAc. The combined extracts were washed with water followed by brine then dried over magnesium sulfate, filtered and concentrated. The resulting crude product can be purified by silica gel chromatography using an appropriate eluant system.

Example 1

Preparation of 3-[4-(3-Chlorophenyl)-2H-pyrazol-3-yl]-1H-pyrrolo[2,3-b]pyridine Hydrochloride

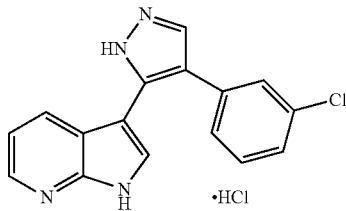 [SMILES: Clc1cccc(-c2cn[nH]c2-c2c[nH]c3ncccc23)c1 ; Cl]

Step 1: Preparation of 2-(3-chlorophenyl)-1-(1-triisopropylsilanyl-1H-pyrrolo[2,3-b]pyridin-3-yl)ethanone. This compound was prepared by the reaction of 3-chlorobenzylmagnesium chloride (0.25 M solution in diethyl ether) with N-methoxy-N-methyl-1-triisopropylsilanyl-1H-pyrrolo[2,3-b]pyridine-3-carboxamide as described in General Method 1. The desired compound was obtained in 94% yield as a viscous clear oil.

$^1$H NMR (CDCl$_3$): δ=8.62 (d, J=7.9 Hz, 1H), 8.31 (d, J=4.1, 1.7 Hz, 1H), 7.98 (s, 1H), 7.33 (s, 1H), 7.31-7.21 (m, 4H), 4.16 (s, 2H), 1.84 (hep, J=7.5 Hz, 3H) and 1.12 ppm (d, J=7.5 Hz, 18H).

Step 2: Preparation of 3-[4-(3-chlorophenyl)-2H-pyrazol-3-yl]-1H-pyrrolo[2,3-b]pyridine hydrochloride. The title compound was prepared by the reaction of 2-(3-chlorophenyl)-1-(1-triisopropylsilanyl-1H-pyrrolo[2,3-b]pyridin-3-yl) ethanone with Bredericks reagent followed by hydrazine monohydrochloride and hydrazine monohydrate as described in General Method 2, Procedure A. The desired compound was obtained in 48% yield as the hydrochloride salt as a pale yellow solid.

$^1$H NMR (CD$_3$OD): δ=8.52 (bs, 1H), 8.50 (bd, J=4.5 Hz, 1H), 8.18 (s, 1H), 7.82 (s, 1H), 7.57 (dd, J=7.9, 6.0 Hz, 1H), 7.41 (bs, 1H), and 7.31 ppm (m, 3H).

m/z=295 [M+H]$^+$

Example 2

Preparation of 3-[4-Phenyl-2H-pyrazol-3-yl]-1H-pyrrolo[2,3-b]pyridine Hydrochloride

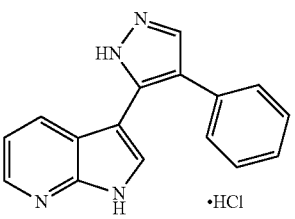 [SMILES: c1ccc(-c2cn[nH]c2-c2c[nH]c3ncccc23)cc1 ; Cl]

Step 1: Preparation of 2-phenyl-1-(1-triisopropylsilanyl-1H-pyrrolo[2,3-b]pyridin-3-yl)-ethanone. This compound was prepared by the reaction of benzylmagnesium chloride (2.0 M solution in THF) with N-methoxy-N-methyl-1-triisopropylsilanyl-1H-pyrrolo[2,3-b]pyridine-3-carboxamide as described in General Method 1. The desired compound was obtained in 92% yield as a light yellow viscous oil.

$^1$H NMR (CDCl$_3$): δ=8.59 (dd, J=7.9, 1.7 Hz, 1H), 8.30 (dd, J=4.7, 1.7 Hz, 1H), 7.90 (s, 1H), 7.36-7.19 (m, 5H), 7.16 (dd, J=7.9, 4.7 Hz, 1H), 4.16 (s, 2H), 1.83 (hep, J=7.5 Hz, 3H) and 1.11 ppm (d, J=7.5 Hz, 18H).

Step 2: Preparation of 3-[4-phenyl-2H-pyrazol-3-yl]-1H-pyrrolo[2,3-b]pyridine hydrochloride. The title compound was prepared by the reaction of 2-(3-chlorophenyl)-1-(1-tri-isopropylsilanyl-1H-pyrrolo[2,3-b]pyridin-3-yl)ethanone with Bredericks reagent followed by hydrazine monohydrochloride and hydrazine monohydrate as described in General Method 2, Procedure A. The desired compound was obtained in 31% yield as the hydrochloride salt as a pale yellow foam.

$^1$H NMR (DMSO-d$_6$): δ=12.97 (bs, 1H), 11.93 (bs, 1H), 8.22 (bs, 1H), 7.88 (bs, 1H), 7.35-7.20 (m, 7H) and 6.99 ppm (bs, 1H).

m/z=261 [M+H]$^+$

Example 3

Preparation of Benzyl-{3-[4-(3-chlorophenyl)-2H-pyrazol-3-yl]-1H-pyrrolo[2,3-b]pyridin-6-yl}amine Dihydrochloride

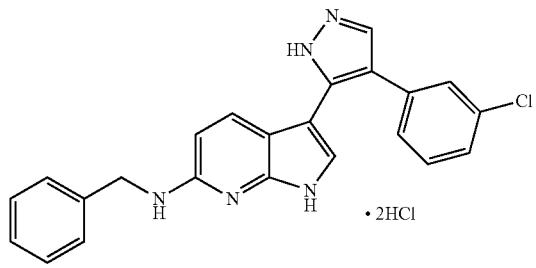 [SMILES: Clc1cccc(-c2cn[nH]c2-c2c[nH]c3nc(NCc4ccccc4)ccc23)c1]

Step 1: Preparation of 3-[4-(3-chlorophenyl)-2H-pyrazol-3-yl]-1H-pyrrolo[2,3-b]pyridine 7-oxide meta-chlorobenzoate salt. A solution of 3-[4-(3-chlorophenyl)-2H-pyrazol-3-yl]-1H-pyrrolo[2,3-b]pyridine (147 mg, 0.5 mmol) in EtOAc (5 mL) was cooled in an ice bath and m-CPBA (148 mg, 0.6 mmol) added in one portion. The resulting suspension was stirred at 0° C. for 3 hours. After this time a second portion of m-CPBA (62 mg, 0.25 mmol) was added and the reaction stirred for an additional 14 hours, during which time the reaction warmed to room temperature. The reaction mixture was then filtered and the solids washed with ethyl acetate (2 mL) and air dried on the pump. This afforded 3-[4-(3-chlorophenyl)-2H-pyrazol-3-yl]-1H-pyrrolo[2,3-b]pyridine 7-oxide meta-chlorobenzoate salt as white solid in 67% yield.

m/z=311 [M+H]$^+$

Step 2: Preparation of benzyl-{3-[4-(3-chlorophenyl)-2H-pyrazol-3-yl]-1H-pyrrolo[2,3-b]-pyridin-6-yl}amine dihydrochloride. A solution of 3-[4-(3-chlorophenyl)-2H-pyrazol-3-yl]-1H-pyrrolo[2,3-b]pyridine 7-oxide meta-chlorobenzoate salt (93 mg, 0.2 mmol), DIPEA (104 mg, 0.8 mmol) and benzylamine (45 mg, 0.4 mmol) in DMF was treated with PyBrOP (186 mg, 0.4 mmol) and the resulting solution stirred at room temperature overnight. After this time the reaction was diluted with EtOAc (150 ml) and washed with saturated sodium bicarbonate solution (2×50 mL) followed by saturated sodium chloride solution (50 mL). The organic layer was then dried over sodium sulfate and concentrated. The residue was purified by column chromatography (SiO$_2$, 40-100% EtOAc in hexanes) followed by further purification by preparative TLC (SiO$_2$, EtOAc). The resulting material was then combined with material obtained from a previous reaction, run under identical conditions, and the combined product treated with 1N HCl/MeOH (1:1, 5 mL). The resulting solution was then concentrated and the residue re-dissolved in water (5 mL). Subsequent isolation by lyophilization afforded the title compound as a white solid in 9% overall yield.

$^1$H NMR (DMSO-d$_6$): δ=13.8 (bs, 1H), 13.3 (s, 1H), 12.2 (bs, 1H), 10.7 (bs, 1H), 8.07 (s, 1H), 7.99 (d, J=6.5 Hz, 1H), 7.46-7.31 (m, 9H), 6.87 (s, 1H), 6.58 (d, J=6.0 Hz, 1H), 7.41 (bs, 1H), and 4.74 ppm (d, J=4.5 Hz, 2H).

m/z=400 [M+H]$^+$

Example 4

Preparation of Benzyl-[3-(4-phenyl-2H-pyrazol-3-yl)-1H-pyrrolo[2,3-b]pyridin-6-yl]amine

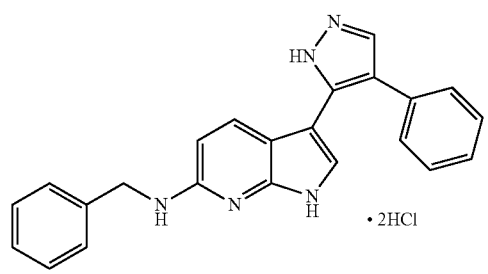 [SMILES: c1ccc(CNc2ccc3c(-c4[nH]ncc4-c4ccccc4)c[nH]c3n2)cc1]

Step 1: Preparation of 3-(4-phenyl-2H-pyrazol-3-yl)-1H-pyrrolo[2,3-b]pyridine 7-oxide meta-chlorobenzoate salt. This material was synthesized by the method described in Step 1 of Example 3 using m-CPBA as oxidant in 53% overall yield.

m/z=277 [M+H]$^+$

Step 2: Preparation of benzyl-[3-(4-phenyl-2H-pyrazol-3-yl)-1H-pyrrolo[2,3-b]pyridin-6-yl]amine dihydrochloride. To a solution of 3-(4-phenyl-2H-pyrazol-3-yl)-1H-pyrrolo[2,3-b]pyridine 7-oxide meta-chlorobenzoate salt (247 mg, 0.57 mmol) in acetonitrile (3 mL) was added dimethylsulfate (124 mg, 0.98 mmol) and the mixture heated to 60° C. for 16 hours. After this time the reaction was cooled to room temperature and benzylamine (490 mg, 4.57 mmol) added. The reaction was then reheated to 55° C. and held at this temperature for 7 hours. Additional benzylamine (245 mg, 2.28 mmol) was then added and heating continued for an additional 17 hours. The mixture was then cooled to room temperature and diluted with EtOAc (50 mL). The organic was then washed with 10% sodium bicarbonate solution (50 mL) and dried over sodium sulfate. Filtration, concentration and purification of the residue by preparative thin layer chromatography afforded an oil. This material was treated with 1.25M Hydrogen Chloride in methanol (5 mL) and the solution concentrated. Trituration of the residue with diethyl ether and isolation of the resulting solids gave the title compound as a light yellow solid in 2% yield.

$^1$H NMR (MeOD): δ=7.95 (bs, 1H), 7.74 (d, J=9.0 Hz, 1H), 7.41-7.21 (m, 10H), 7.17 (s, 1H), 6.54 (d, J=9.0 Hz, 1H) and 4.62 ppm (s, 2H).

m/z=366 [M+H]$^+$

Example 5

Preparation of 2-(Benzyl-{3-[4-(3-chlorophenyl)-2H-pyrazol-3-yl]-1H-pyrrolo[2,3-b]pyridin-6-yl}amino)ethanol Dihydrochloride

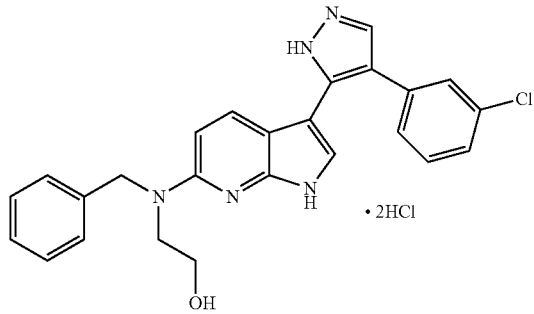 [SMILES: OCCN(Cc1ccccc1)c1ccc2c(-c3[nH]ncc3-c3cccc(Cl)c3)c[nH]c2n1]

Step 1: Preparation of N-benzyl-N-(2-((tert-butyldimethylsilyl)oxy)ethyl)-3-(4-(3-chlorophenyl)-1H-pyrazol-5-yl)-1H-pyrrolo[2,3-b]pyridin-6-amine. This material was synthesized by the PyBrOP mediated amination of 3-(4-phenyl-2H-pyrazol-3-yl)-1H-pyrrolo[2,3-b]pyridine 7-oxide meta-chlorobenzoate salt with 2-((tert-butyldimethylsilyl)oxy)ethylamine as described in Step 2 of Example 4. The crude product obtained was used directly in Step 2 below.

m/z=558 [M+H]$^+$

Step 2: Preparation of 2-(benzyl-{3-[4-(3-chlorophenyl)-2H-pyrazol-3-yl]-1H-pyrrolo[2,3-b]pyridin-6-yl}amino)ethanol dihydrochloride. To a solution of crude N-benzyl-N-(2-((tert-butyldimethylsilyl)oxy)ethyl)-3-(4-(3-chlorophenyl)-1H-pyrazol-5-yl)-1H-pyrrolo[2,3-b]pyridin-6-amine (78 mg, 0.14 mmol) in methanol (5 mL) was added a 4M solution of hydrogen chloride in dioxane (5 mL, 20 mmol) and the solution stirred at room temperature for 2 hours. After this time the reaction was concentrated and the residue purified by preparative HPLC. Concentration of the product containing fractions afforded a solid that was re-dissolved in MeOH (5 mL) and treated with 2N HCl (2 mL). The solution was then re-concentrated, the residue co-evaporated with acetonitrile (5 mL) then dissolved in water (5 mL). Subsequent isolation by lyophilization afforded the title compound as a yellow solid in 25% yield over 2 steps.

$^1$H NMR (DMSO-d$_6$): δ=12.1 (bs, 1H), 8.11 (s, 1H), 7.94 (d, J=5.1 Hz, 1H), 7.33-7.02 (m, 9H), 7.00 (d, J=6.5 Hz, 2H), 4.48 (s, 2H), 3.46 (bs, 2H) and 3.36 ppm (bs, 2H)

m/z=444 [M+H]$^+$

Example 6

Preparation of 2-{Benzyl-[3-(4-phenyl-2H-pyrazol-3-yl)-1H-pyrrolo[2,3-b]pyridin-6-yl]-amino}ethanol Dihydrochloride

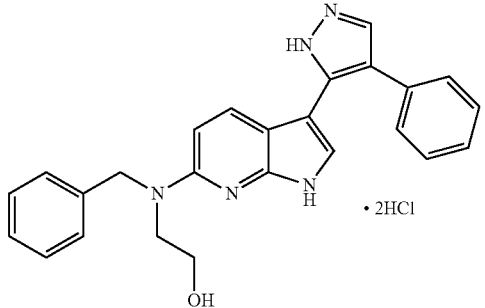 [SMILES: OCCN(Cc1ccccc1)c1ccc2c(-c3[nH]ncc3-c3ccccc3)c[nH]c2n1]

Step 1: Preparation of N-benzyl-N-(2-((tert-butyldimethylsilyl)oxy)ethyl)-3-(4-phenyl-1H-pyrazol-5-yl)-1H-pyrrolo[2,3-b]pyridin-6-amine. This material was synthesized by the PyBrOP mediated amination of 3-(4-phenyl-2H-pyrazol-3-yl)-1H-pyrrolo[2,3-b]pyridine 7-oxide meta-chlorobenzoate salt with 2-((tert-butyldimethylsilyl)oxy)ethylamine as described in Step 2 of Example 4. The crude product obtained was used directly in Step 2 below.

m/z=524 [M+H]$^+$

Step 2: Preparation of 2-{benzyl-[3-(4-phenyl-2H-pyrazol-3-yl)-1H-pyrrolo[2,3-b]pyridin-6-yl]-amino}ethanol dihydrochloride. The title compound was synthesized by the hydrogen chloride mediated deprotection of N-benzyl-N-(2-((tert-butyldimethylsilyl)oxy)ethyl)-3-(4-phenyl-1H-pyrazol-5-yl)-1H-pyrrolo[2,3-b]pyridin-6-amine as described in Step 2 of Example 5. Purification by preparative TLC then preparative HPLC, followed by salt formation with 2N HCl/MeOH and final isolation by lyophilization from water afforded 2-{benzyl-[3-(4-phenyl-2H-pyrazol-3-yl)-1H-pyrrolo[2,3-b]pyridin-6-yl]-amino}ethanol dihydrochloride in 10% overall yield as a yellow solid.

$^1$H NMR (DMSO-d$_6$): δ=11.6 (bs, 1H), 7.98 (s, 1H), 7.88 (d, J=4.0 Hz, 1H), 7.23-7.02 (m, 11H), 6.86 (d, J=5.0 Hz, 1H), 4.43 (s, 2H), 3.41 (t, J=5.5 Hz, 2H) and 3.36 ppm (bs, 2H).

m/z=366 [M+H]$^+$

Example 7

Assay of Compounds of the Invention Against ERK-2

Compounds of the invention were assayed for ability to inhibit ERK-2 kinase using a 33-P radio-ligand binding assay. 33-P labeled ATP was used as the radio-ligand and myelin basic protein was used as the substrate. A non-labeled ATP concentration of 1 μM was used. Plates were incubated at 22° C. before isolation and radioactivity determination by scintillation counting. The IC$_{50}$ values (concentration causing a half-maximal inhibition) and Hill coefficients (nH) were determined by non-linear regression analysis of competition curves generated with 10 data points using Hill equation curve fitting. Compounds of the invention inhibited ERK-2 activity with IC$_{50}$ values delineated in Table 1.

TABLE 1

| Example | IC$_{50}$ (μM) |
| --- | --- |
| 1 | 1.43 |
| 2 | 9.86 |
| 3 | 2.23 |
| 4 | 11.3 |

Example 8

Assay of Compounds of the Invention to Inhibit Keratinocyte Proliferation

Compounds of the Invention were assayed for their ability to inhibit the proliferation of human keratinocytes. Namely, keratinocytes were plated on day zero and allowed to attach. One day later, the cells were washed and then treated with control culture medium with or without the test compound. Cells were harvested and counted on day-2. Value for the time-zero control was determined (mean and standard deviation based on triplicate experiments with n=9 data points). The untreated control value at day 2 was then determined (mean and standard deviation based on triplicate experiments with n=12 data points). All of the values from treated samples were compared to the control values and are expressed as the change from control±the standard deviation based on the three experiments. Observed results for Example 1 are displayed in Table 2 below. From these data it was calculated that Example 1 inhibited the proliferation of keratinocytes with a $GI_{50}$ of 4.36 μM. Graphical representation of these data is given in FIG. 1.

TABLE 2

| Test Concentration (μM) | Inhibition (%) |
|---|---|
| 0.03 | −20 |
| 0.15 | −13 |
| 0.30 | −6 |
| 1.51 | 8 |
| 3.02 | 21 |
| 6.04 | 72 |
| 15.1 | 118 |

Example 9

Figure 2:
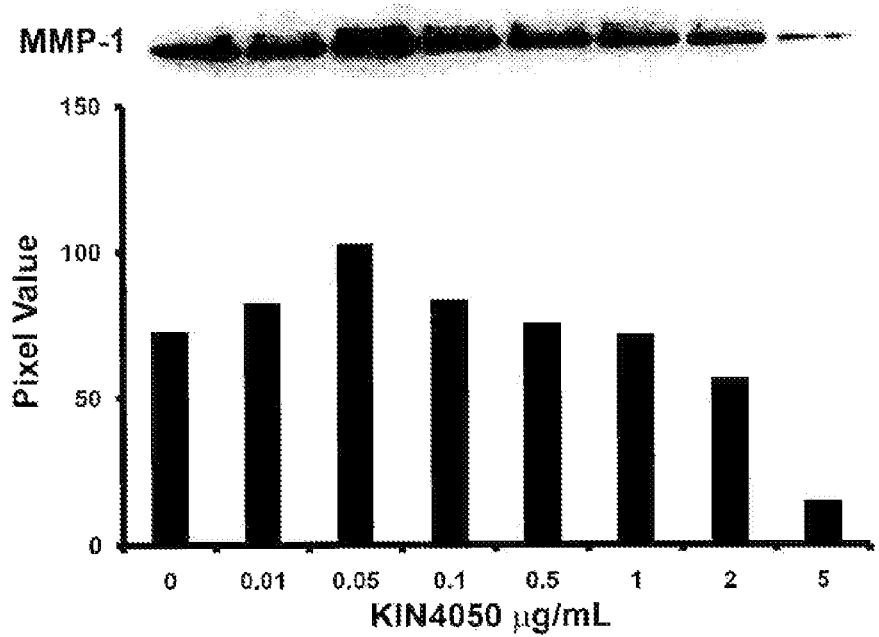
FIG. 2 is a graph which demonstrates the effect of an embodiment of the invention on MMP-1 production in skin fibroblasts.

Ability of Compounds of the Invention to Inhibit MMP-1 Expression in Skin Fibroblasts Fibroblasts were plated on day zero and allowed to attach. One day later, the cells were washed and then treated with control culture medium with or without test compound. Cells were harvested and counted on day-3. The culture medium was then assayed via Western blot analysis to determine expression levels of MMP-1. Results from this analysis are shown in FIG. 2. From this analysis it is apparent that at a concentration of 5 μg/mL Example 1 significantly inhibited MMP-1 expression in skin fibroblast cells.

TABLE 3

Compounds

| Target | $R^{10}$ | $R^3$ | $R^4$ | m | X | $R^5$ | $R^6$ |
|---|---|---|---|---|---|---|---|
| 1 | Me | H | H | 1 | O | H | n/a |
| 2 | Bn | H | H | 1 | O | H | n/a |
| 3 | Ph | H | H | 1 | O | H | n/a |
| 4 | 4-MeO—Ph | H | H | 1 | O | H | n/a |
| 5 | 4-F—Ph | H | H | 1 | O | H | n/a |
| 6 | $CH_2CH_2OH$ | H | H | 1 | O | H | n/a |
| 7 | 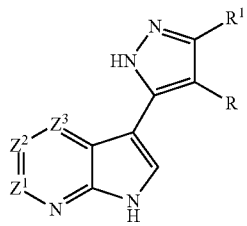 | H | 1 | C | =O | OH | |
| 8 | H | H | H | 1 | O | H | n/a |
| 9 | H | Me | H | 1 | O | H | n/a |
| 10 | H | H | Me | 1 | O | H | n/a |
| 11 | tert-Bu | H | H | 1 | O | H | n/a |
| 12 | Me | H | H | 2 | O | H | n/a |
| 13 | Bn | H | H | 2 | O | H | n/a |

TABLE 3-continued

Compounds

| Target | $R^{10}$ | $R^3$ | $R^4$ | m | X | $R^5$ | $R^6$ |
|---|---|---|---|---|---|---|---|
| 14 | H | H | H | 2 | O | H | n/a |
| 15 | Me | H | H | 2 | C | =O | OH |
| 16 | Me | H | H | 3 | O | H | n/a |
| 17 | Bn | H | H | 3 | O | H | n/a |
| 18 | H | H | H | 3 | O | H | n/a |
| 19 | Me | H | H | 1 | N | Me | Me |
| 20 | Bn | H | H | 1 | N | Me | Me |
| 21 | H | H | H | 1 | N | morpholino | |
| 22 | H | H | H | 1 | N | N-methylpiperazino | |
| 23 | Me | H | H | 1 | N | morpholino | |
| 24 | Bn | H | H | 1 | N | morpholino | |

The invention claimed is:

1. A compound of formula I:

wherein
R is selected from hydrogen, $(C_1-C_{12})$hydrocarbon, $(C_3-C_{10})$carbocycle and heteroaryl, each of which may be optionally substituted by one or more substituents selected from hydrogen, $(C_1-C_6)$hydrocarbon, halogen, $(C_1-C_6)$alkoxy and $(C_1-C_6)$alkylthio;
$R^1$ is hydrogen or $(C_1-C_6)$hydrocarbon;
$Z^1$ is $CR^a$;
$Z^2$ and $Z^3$ are each chosen independently from N and $CR^a$;

$R^a$ is chosen independently in each occurrence from hydrogen, $(C_1\text{-}C_6)$alkyl and $(CR^3R^4)_n\text{—}R^2$, wherein one or more $CR^3R^4$ may be replaced by O, $NR^{10}$, S or C=O;

$R^2$ is $OR^5$ or $NR^5R^6$;

$R^3$ is independently selected from hydrogen and $(C_1\text{-}C_6)$ hydrocarbon;

$R^4$ is independently selected from hydrogen and $(C_1\text{-}C_6)$ hydrocarbon;

$R^5$ is independently selected from hydrogen and $(C_1\text{-}C_6)$ hydrocarbon;

$R^6$ is independently selected from hydrogen and $(C_1\text{-}C_6)$ hydrocarbon, or $R^5$ and $R^6$, together with the nitrogen to which they are attached, may form a 3- to 10-membered monocyclic or bicyclic heterocycle;

$R^{10}$ is selected from hydrogen and a $(C_1\text{-}C_{10})$hydrocarbon optionally substituted with halogen, $(C_1\text{-}C_6)$ alkyl, $(C_1\text{-}C_6)$alkoxy or hydroxy$(C_1\text{-}C_6)$alkyl; or $R^3$ and $R^{10}$, together with the nitrogen to which they are attached, may form a 3- to 10-membered monocyclic or bicyclic heterocycle; and n is selected from 1, 2, 3, 4, 5, 6, 7, 8 and 9.

2. A compound according to claim 1 wherein R is phenyl optionally substituted with halogen or methyl.

3. A compound according to claim 2 wherein R is 3-chlorophenyl.

4. A compound according to claim 1 wherein $Z^1$, $Z^2$ and $Z^3$ are each $CR^a$.

5. A compound according to claim 4 wherein $Z^2$ and $Z^3$ are each CH.

6. A compound according to claim 5 wherein $Z^1$ is CH, C—W—$(CR^3R^4)_n$OH or C—W—$(CR^3R^4)_n$NH$_2$, wherein W is selected from O, $NR^{10}$, S and C=O.

7. A compound according to claim 6 wherein W is NH.

8. A compound according to claim 1 of formula Ia

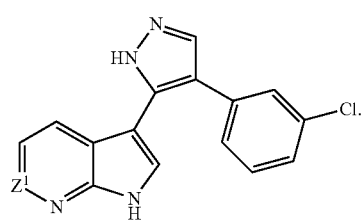

Ia

9. A compound according to claim 8 wherein $Z^1$ is CH, C—W—$(CR^3R^4)_n$OH or C—W—$(CR^3R^4)_n$NH$_2$, wherein W is selected from O, $NR^{10}$, S and C=O.

10. A pharmaceutical composition comprising at least one compound of claim 1 and a pharmaceutically acceptable carrier.

11. A process for preparing a compound of formula III

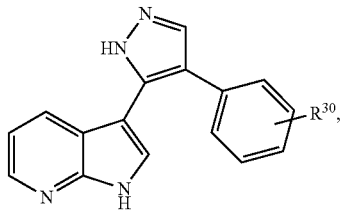

III said process comprising the steps of:

a) reacting a compound of formula IV

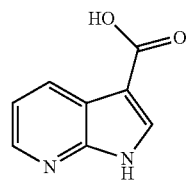

IV with CH$_3$NHOCH$_3$ and TIPS-Cl to form a compound of formula V

V b) reacting a compound of formula V with a compound of formula VI

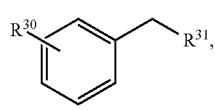

VI wherein $R^{30}$ is selected from halogen and methyl, and $R^{31}$ is selected from Cl, Br, I, toluenesulfonyl, benzenesulfonyl, methanesulfonyl and triflate to form a compound of formula VII

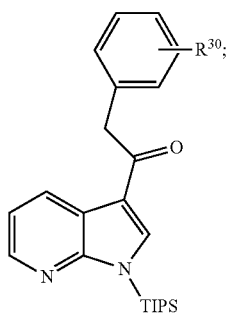

VII c) reacting a compound of formula VII with Brederecks Reagent and hydrazine and cleaving with acid to form a compound of formula III.

12. A process according to claim 11 wherein the reaction of a compound of formula IV and $CH_3NHOCH_3$ is carried out in the presence of a diimide and 1-hydroxy-1H-benzotriazole.

13. A process for preparing a compound of formula VIII

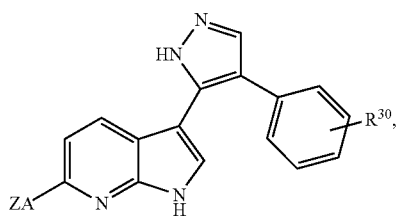

VIII wherein A is selected from O, S and $NR^{32}$;

Z is chosen from hydrogen, $(C_1-C_6)$alkyl and $[(C_1-C_{10})$ alkyl$]-R^8$, wherein one or more $CH_2$ of the alkyl may be replaced by O, $NR^{10}$, S or C=O, and wherein $R^8$ is protected OH or protected $NHR^{11}$;

$R^{10}$ and $R^{11}$ are independently selected in each instance from hydrogen and $(C_1-C_6)$alkyl; and $R^{30}$ is selected from halogen and methyl $R^{32}$ is hydrogen or a $(C_1-C_6)$ hydrocarbon;

comprising the steps of a) reacting a compound of formula III

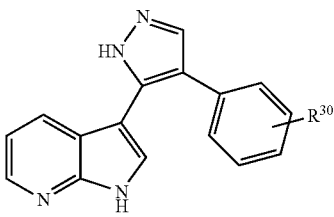

III with an oxidant to form a compound of formula IX

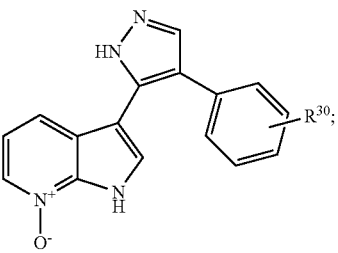

IX b) reacting a compound of formula IX with an activating agent to form a compound of formula X

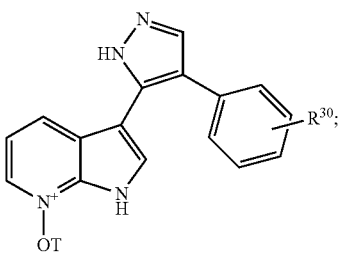

X and c) reacting a compound of formula X with H-AZ to form a compound of formula VIII, wherein A and Z are defined as above.

14. A process according to claim 12 wherein the oxidant is m-CPBA and the activating agent is dimethylsulfate or PyBrOP.

* * * * *

UNITED STATES PATENT AND TRADEMARK OFFICE
CERTIFICATE OF CORRECTION

| | |
|---|---|
| PATENT NO. | : 8,697,697 B2 |
| APPLICATION NO. | : 13/977948 |
| DATED | : April 15, 2014 |
| INVENTOR(S) | : Fairfax et al. |

Page 1 of 1

It is certified that error appears in the above-identified patent and that said Letters Patent is hereby corrected as shown below:

In the Claims:

Column 26, Line 46: Claim 14, Delete "claim 12" and insert -- claim 13 --

Signed and Sealed this
Eighth Day of July, 2014

Michelle K. Lee
*Deputy Director of the United States Patent and Trademark Office*